US006424731B1

(12) United States Patent
Launay et al.

(10) Patent No.: US 6,424,731 B1
(45) Date of Patent: Jul. 23, 2002

(54) METHOD OF POSITIONING A RADIOGRAPHIC DEVICE

(75) Inventors: Laurant Launay, Versailles; Yves Lucien Marie Trousset, Palaiseau; Régis Vaillant, Villebon sur Yvette; Réne Romeas, Palaiseau, all of (FR)

(73) Assignee: GE Medical Systems S.A. (FR)

( * ) Notice: Subject to any disclaimer, the term of this patent is extended or adjusted under 35 U.S.C. 154(b) by 0 days.

(21) Appl. No.: 09/362,078

(22) Filed: Jul. 27, 1999

(30) Foreign Application Priority Data

Jul. 17, 1998 (FR) ............................................ 98 09159

(51) Int. Cl.[7] ................................................ G06K 9/00
(52) U.S. Cl. ...................................................... 382/128
(58) Field of Search ................................ 382/128, 130, 382/132, 154, 285; 378/1, 6, 20, 22, 42, 44, 46, 47, 68, 87, 162, 163, 165, 195, 196, 205; 702/28, 40, 8; 250/581, 582, 583, 587, 206.2, 227.29, 559.19; 604/20, 21; 600/160; 606/97

(56) References Cited

U.S. PATENT DOCUMENTS

| | | | |
|---|---|---|---|
| 4,649,277 A | | 3/1987 | Terra et al. ................. 382/130 |
| 5,247,555 A | * | 9/1993 | Moore et al. ................... 378/4 |
| 5,515,416 A | * | 5/1996 | Siczek et al. ................ 378/197 |
| 5,699,446 A | | 12/1997 | Rougee et al. ............... 382/130 |
| 6,052,618 A | * | 4/2000 | Dahlke et al. ............... 600/523 |
| 6,079,876 A | * | 6/2000 | Schuetz ........................ 378/205 |
| 6,149,592 A | * | 11/2000 | Yanof et al. ................. 600/427 |
| 6,236,708 B1 | * | 5/2001 | Lin et al. ....................... 378/22 |
| 6,285,738 B1 | * | 9/2001 | Nagai et al. ................ 378/98.8 |

FOREIGN PATENT DOCUMENTS

| | | | |
|---|---|---|---|
| WO | 91186444 | 12/1991 | ............ A61N/5/00 |
| WO | 9724697 | 7/1997 | ............ G06T/17/40 |

* cited by examiner

*Primary Examiner*—Andrew W. Johns
*Assistant Examiner*—Shervin Nakhjavan
(74) *Attorney, Agent, or Firm*—Jay L. Chaskin

(57) ABSTRACT

Method of controlling of a radiology device, of the type comprising a means of emission of an X-ray beam and a means of reception of the X-ray beam, after it has crossed a part of the object's body, in which a three-dimensional image of a part of the object's body is reconstructed from a series of two-dimensional films, two-dimensional views of the three-dimensional image are produced at different angles of incidence, the angle of incidence allowing the best visualization of the part of the object's body are selected, the angles of incidence are stored in memory, and the angles of incidence are supplied to the radiology device for its positioning with a view to an intervention or procedure on the part of the object's body under fluoroscopy allowing a visualization in real time of two-dimensional.

14 Claims, 2 Drawing Sheets

METHOD OF POSITIONING A RADIOGRAPHIC DEVICE

BACKGROUND OF THE INVENTION

The present invention is directed to a method of positioning a radiology device.

Radiology devices generally comprise a tube for emitting an X-ray beam in a given direction, means for positioning at least one part of an object's body in the X-ray beam, and X-ray sensitive means of reception of the beam after it crosses that part of the object's body.

In angiography applications, for example, the blood vessels of a human body have the same absorption as the tissues surrounding them are thus invisible on the images obtained. An image is first taken without addition of a contrast medium, then an iodine-base contrast medium, for example, is injected into the blood of the human body, and a second image is taken after the contrast medium is properly distributed in the vascular system of the human body. The two images or series of images obtained being digitized by electronic means, an image subtraction is then carried out, making it possible to take away from the second image the organs visible on the first, that is, the organs naturally visible to X-rays, such as bones, etc.

It is known how to carry out two-dimensional vascular angiography. Now, it is very difficult to locate significant features such aneurysms, notably cerebral, which can be masked by other vessels or organs, by reason of the complexity of the extreme tangle of structures having to be visualized. If the operator manages to carry out this location, it is then difficult to visualize the features satisfactorily in order to determine their importance and/or gravity and, if necessary, the best way of attending to them. The operator is therefore led to repeat two-dimensional films at angles of incidence chosen at random or based on the operator's own experience, which tends to increase the X-ray dose received by the human body and to make the success of angiography depend on the know-how of a given operator.

Methods of image acquisition with rotational positioning of the radiology device are also known. An image is acquired for each of the different angles of incidence. The images thus obtained can be treated, notably, by algorithms of the type used in computerized axial tomography to make a volume reconstruction of a system of arteries and veins. Depending on what the films taken at the first angles of incidence reveal, other acquisitions are made at new angles of incidence, which make possible a closer observation of the region concerned. The choice of those angles of incidence in space is difficult also by reason of the complexity of the region observed and because of the possible superposition of other vessels.

The angiography systems with three axes of rotation offer the possibility of making rotational dynamic acquisitions according to each of the axes in space. However, their possibilities remain poorly utilized because of the difficulty of their use, due to the fact that the three-dimensional orientation of the vessels is a priori unknown.

U.S. Pat. No. 5,699,446 proposes a method of image by positioning the radiology device to determine the best angles of incidence and, in particular, for positioning the detector parallel to the object having to be visualized. Two acquired reference images are used for that purpose at two different angles of incidence, in order to determine automatically the three-dimensional orientation of the vessel having to be examined. A triaxial apparatus is used, from determination of the angular positions of the first two axes, to position the third axis in a position parallel to the vessels. The rotation on the third axis is freely used to make the acquisitions.

Assisted by epipolar lines, the operator designates a segment on each view. The segment can then be reconstructed in three dimensions and an incidence proposed, so that the direction of the X-ray beam will be perpendicular to that segment. This method requires numerous manipulations and does not guarantee that the final incidence supplied will offer the best possible view of the organ.

BRIEF SUMMARY OF THE INVENTION

The present invention is directed to a method for obtaining a specific image or images of a part an object body, e.g., a human body.

The method, according to an embodiment of the invention, is intended for a radiology device of the type comprising a means of emission of an X-ray beam and a means of reception of the X-ray beam, after it has crossed a part of the object's body. A three-dimensional image of a part of the object's body is reconstructed from a series of two-dimensional films. Two-dimensional views of the three-dimensional image are produced at different angles of incidences. The angles of incidence making possible the best visualization of the part of the object's body are selected. The angles of incidence are stored in a memory.

The angles incidence are supplied to the radiology device for its positioning with a view to an intervention or procedure on the part of the object's body under fluoroscopy allowing visualization in real time of two-dimensional films. The best angle of incidence found can thus found for monitoring the progress of the intervention or procedure.

In one embodiment of the invention, the memorization of the angles of incidence is stored in a radiology device memory.

The angles of incidence are advantageously supplied to the radiology device automatically.

In one embodiment of the invention the selection of the angles of incidence are made by processing of the three-dimensional image.

In another embodiment of the invention, the selection of the images is made by processing the angles of visualization of the three-dimensional image.

In order to avoid the risk of the radiology device striking the object's body, it may be prevented from being positioned at angles where such risk might occur.

BRIEF DESCRIPTION OF THE DRAWINGS

The present invention will be better understood by studying the detailed description of an embodiment taken by way, of nonlimitative example and illustrated by the attached drawings, wherein.

DETAILED DESCRIPTION OF THE INVENTION

Figure 1:
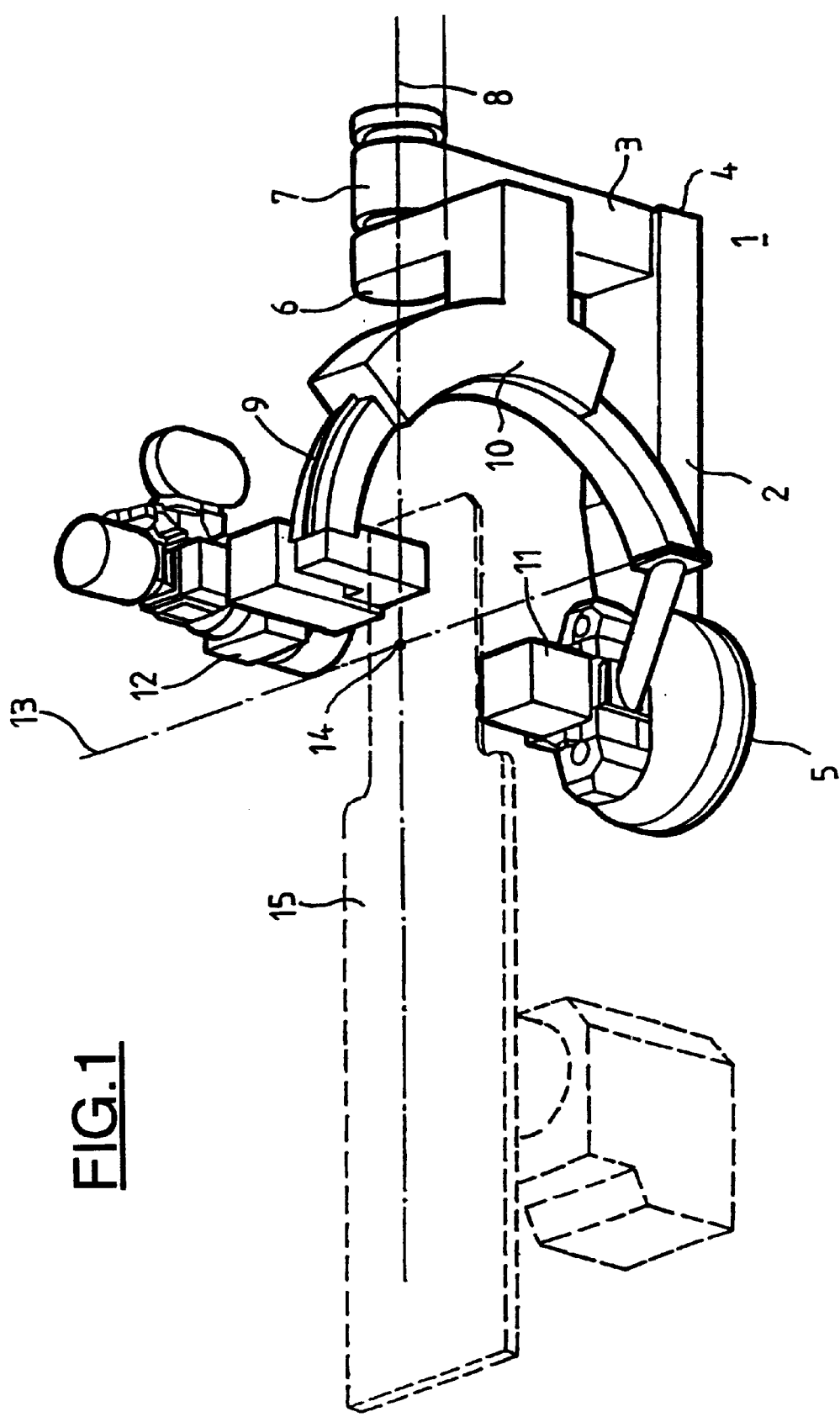
FIG. 1 is a two-dimensional view of a three-axis radiology device which can be used to apply the method according to an embodiment of the invention.

As can be seen in FIG. 1, the radiology device comprises an L-shaped stand with a substantially horizontal base 2 and a substantially vertical support 3 attached to one end 4 of the base 2. At the opposite end 5, the base 2 comprises an axis of rotation parallel to the support 3 and on which the stand is capable of turning. A support arm 6 is attached at a first end to the top 7 of the support 3, rotating on an axis 8. The support arm 6 can be bayonet-shaped. A C-shaped circular arm 9 is maintained by another end 10 of the support arm 6. The C-shaped arm 9 is capable of sliding in rotation on an axis 13 relative to the end 10 of the support arm 6.

The C-shaped arm 9 supports an X-ray tube 11 and an X-ray detector 12 in diametrically opposite facing positions. The detector 12 contains a flat detection surface. The direction of the X-ray beam is determined by a straight line joining a focal point of the tube 11 with the center of the flat surface of the detector 12. The three axes of rotation of the stand 1, support arm 6 and C-shaped arm 9 are secant at a point 14. In mid-position, these three axes are perpendicular to one another.

A table 15, provided to receive an object possesses a longitudinal orientation with the axis 8 in rest position.

In an embodiment of to the invention, a set of images of a blood vessel is acquired for different positions of the radiology device. The three-dimensional image is then reconstructed from a set of two-dimensional images. Two-dimensional views of the three-dimensional image are produced interactively by virtually rotating the three-dimensional image of the vessel in all desired directions until obtaining the view enabling the operator to visualize as well as possible the area of interest, the aneurysm, for example. The position of the radiology device is so determined that the direction of the X-ray beam relative to the vessels is parallel to the direction of visualization of the beam relative to the three-dimensional image.

The last step can be carried out in two ways. One way is manually, with the angles characterizing the position of the radiology device being supplied in real time on the two-dimensional view produced when the operator rotates the three-dimensional image of the vessel. When the best view is determined, the operator supplies those angles of incidence to the radiology device, which is generally equipped with a control lever, in order to reach the position corresponding to that view. This position can be specified, for example, either by anatomical angles, two angles, left/right and cranial/caudal, describing the position of the radiology device in relation to the object, or at angles relative to the radiology device, at least two angles describing the angular motion applied to the radiology device to reach the desired position corresponding to the two-dimensional view selected. The other way is automatically, the angles characterizing the position of the radiology device being calculated and transmitted automatically to the radiology device, so that the operator then no longer has to work the controls, generally the control lever of the radiology device.

However, some angles of incidence of the organ to be visualized cannot be reached physically by the radiology device, because the positioning of the radiology device at those angles of incidence would cause the device to collide with the object's body. To avoid such an accident, the angles at which a collision would be likely to occur are determined in advance and a comparison is made between those predetermined angles and the angles of incidence of the two-dimensional view selected by the operator, in order to issue a warning message if those angles correspond. The operator can then choose another two-dimensional image.

Figure 2:
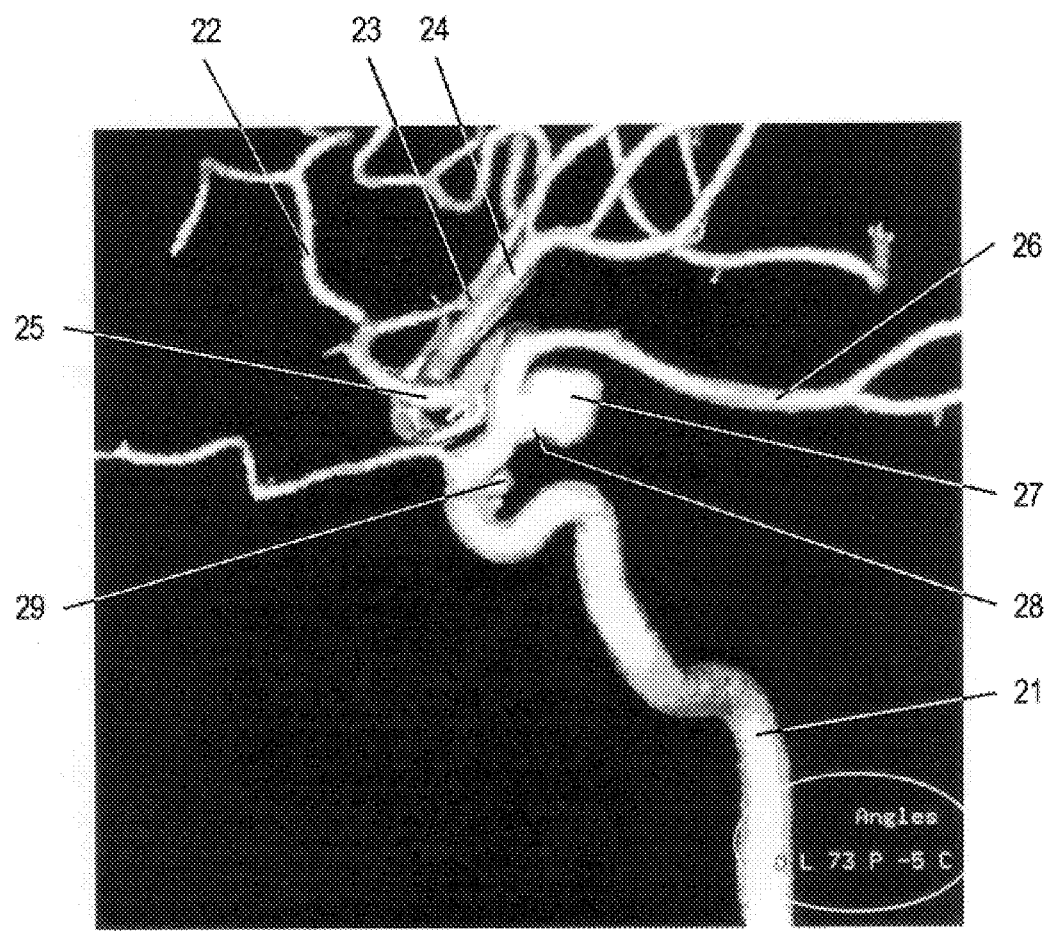
FIG. 2 is a two-dimensional view of an aneurysm visualized according to an embodiment of the method of the invention.

A large-diameter blood vessel 21 and a plurality of small-diameter blood vessels 22 to 26 can be seen in FIG. 2. An aneurysm 27 is found on blood vessel 21 and has a neck 28 forming the junction between the blood vessel 21 and the aneurysm 27 proper and has a smaller diameter than the latter. This two-dimensional view was the best one obtained of the aneurysm 27 in that it enables its neck 28 to be visualized well, which makes it possible to choose the procedure best suited to its neutralization.

A small-sized aneurysm, barely visible in FIG. 2, bears reference 29. Aneurysm 29 can be located on the figure but cannot be satisfactorily visualized for an operation. It would be advisable to choose other angles of incidence in order to visualize its shape properly. In fact, the aneurysm 29 risks being partly concealed by the blood vessel 21 from which it was formed.

At other angles of incidence, it is conceivable that the blood vessel 26 could be in the fore-ground in front of the aneurysm 27 and hide the latter. It can also be seen that blood vessels 23 and 24 seem to be adjacent, when they can very well be offset in the depth direction, which only a two-dimensional image at another angle of incidence will make it possible to determine. At the lower right-hand corner of the view, three angles of incidence are displayed for the operator's information and also the entry of the values of the angles in the memory of the radiology device in case of a manual method. For a better visualization of an object, aneurysm 27, for example, a region of the blood vessel 26 which is to be removed from the three-dimensional image could be defined. Angles of incidences other than that of FIG. 2 could then prove effective for visualizing the aneurysm 27 in two-dimensional view.

The method according to the invention makes it possible to determine a priori and to obtain under fluoroscopy the best possible view-point of an organ. This method enables radiologists or radiology operators to save a great deal of time. In neuroradiology operations or procedures, particularly for the embolization of aneurysms, it considerably improves the safety and reliability of such a therapeutic procedure.

Various modifications in structure and/or steps and/or function may be made by one skilled in the art to the disclosed embodiments without departing from the scope and extent of the invention.

What is claimed is:

1. A method of controlling a radiology device, of the type comprising a means of emission of an X-ray beam and a means of reception of the X-ray beam, after it has crossed a part of the object's body, in which a three-dimensional image of a part of the object's body is reconstructed from a series of two-dimensional films, two-dimensional views of the three-dimensional image are produced at different angles of incidence, the angles of incidence facilitating the best visualization of the part of the object's body are selected, the angles of incidence are stored, and the angles of incidence are supplied to the radiology device for positioning with a view to an intervention or procedure on the part of the object's body under fluoroscopy allowing a visualization in real-time of two-dimensional images.

2. The method according to claim 1, wherein the storing of the angles of incidence is in a memory of the radiology device.

3. The method according to claim 2, wherein the angles of incidence are supplied to the radiology device automatically.

4. The method according to claim 3, wherein the radiology device is prevented from being positioned at angles where there is a risk of its striking the object's body.

5. The method according to claim 2, wherein the angles of incidence are selected by processing of the three-dimensional image.

6. The method according to claim 2, wherein the selection of the angles of incidence is selected by processing of the angles of visualization of the three-dimensional image.

7. The method according to claim 2, wherein the radiology device is prevented from being positioned at angles where there is a risk of its striking the object's body.

8. The method according to claim 1, wherein the angles of incidence are supplied to the radiology device automatically.

9. The method according to claim 8, wherein the angles of incidence are selected by processing of the three-dimensional image.

10. The method according to claim 8, wherein the radiology device is prevented from being positioned at angles where there is a risk of its striking the object's body.

11. The method according to claim 1, wherein the angles of incidence are selected by processing of the three-dimensional image.

12. The method according to claim 11, wherein the radiology device is prevented from being positioned at angles where there is a risk of its striking the object's body.

13. The method according to claim 1, wherein the selection of the angles of incidence is selected by processing of the angles of visualization of the three-dimensional image.

14. The method according to claim 1, wherein the radiology device is prevented from being positioned at angles where there is a risk of its striking the object's body.

* * * * *